United States Patent [19]

Adams et al.

[11] Patent Number: 4,857,508
[45] Date of Patent: Aug. 15, 1989

[54] NOVEL PLATELET-AGGREGATION INHIBITOR PEPTIDE DERIVATIVES

[75] Inventors: Steven P. Adams, St. Charles, Mo.; Larry P. Feigen, Wauconda; Masateru Miyano, Northbrook, both of Ill.

[73] Assignees: Monsanto Company, St. Louis, Mo.; G. D. Searle & Co., Skokie, Ill.

[21] Appl. No.: 128,379

[22] Filed: Dec. 3, 1987

[51] Int. Cl.$^4$ .................. A61K 37/20; C07K 5/10
[52] U.S. Cl. ........................... 514/18; 530/330
[58] Field of Search ........................... 530/330; 514/18

[56] References Cited

U.S. PATENT DOCUMENTS

| 3,795,667 | 3/1974 | Ondetti | 530/330 |
| 4,517,686 | 5/1985 | Ruoslahti et al. | 3/1 |
| 4,578,079 | 3/1986 | Ruoslahti et al. | 530/330 |
| 4,589,881 | 5/1986 | Pierschbacher et al. | 623/11 |
| 4,590,003 | 5/1986 | Twardzik | 530/330 |
| 4,596,790 | 6/1986 | Trygstad et al. | 530/330 |
| 4,614,517 | 9/1986 | Ruoslahti et al. | 530/330 |
| 4,661,111 | 4/1987 | Ruoslahti et al. | 623/11 |
| 4,683,291 | 7/1987 | Zimmerman et al. | 530/330 |

OTHER PUBLICATIONS

Kloczewiak et al., Biochem. 23, 1767–1774 (1984).
Plow et al., Proc. Natl. Acad. Sci. 82, 8057–8061 (1985).
Ruggeri et al., Ibid. 83, 5708–5712 (1986).
Ginsberg et al., J. Biol. Chem. 260(7), 3931–3936 (1985).
Haverstick et al., Blood 66(4) 946–952 (1985).

Primary Examiner—Lester L. Lee
Attorney, Agent, or Firm—Scott J. Meyer; James W. Williams, Jr.

[57] ABSTRACT

Novel tetrapeptide derivatives are provided which have useful activity as inhibitors of platelet aggregation. These compounds have the sequence X-Gly-Asp-Y wherein X is illustrated by arginine and Y is illustrated by O-methyltyrosine amide.

16 Claims, No Drawings

NOVEL PLATELET-AGGREGATION INHIBITOR PEPTIDE DERIVATIVES

BACKGROUND OF THE INVENTION

This invention relates to novel peptide derivatives and more particularly to tetrapeptide derivatives having activity as inhibitors of platelet aggregation.

Fibrinogen is a glycoprotein present as a normal component of blood plasma. It participates in platelet aggregation and fibrin formation in the blood clotting mechanism.

Platelets are cellular elements found in whole blood which also participate in blood coagulation. Fibrinogen binding to platelets is important to normal platelet function in the blood coagulation mechanism. When a blood vessel receives an injury, the platelets binding to fibrinogen will initiate aggregation and form a thrombus. Interaction of fibrinogen with platelets occurs through a membrane glycoprotein complex, known as gpIIb/IIIa; this is an important feature of the platelet function. Inhibitors of this interaction are useful in modulating platelet thrombus formation.

It is also known that another large glycoprotein named fibronectin, which is a major extracellular matrix protein, interacts with fibrinogen and fibrin, and with other structural molecules such as actin, collagen and proteoglycans. Various relatively large polypeptide fragments in the cell-binding domain of fibronectin have been found to have cell-attachment activity. See U.S. Pat. Nos. 4,517,686; 4,589,881; and 4,661,111. These polypeptides include an internal amino acid sequence Arg-Gly-Asp-Ser. Certain relatively short peptide fragments from the same molecule were found to promote cell attachment to a substrate when immobilized on the substrate or to inhibit attachment when in a solubilized or suspended form. See U.S. Pat. Nos. 4,578,079 and 4,614,517. These peptides were defined as X-Arg-Gly-Asp-R-Y wherein X=H or amino acid,
R=Thr or Cys;
and
X-Arg-Gly-Asp-Ser-Y
wherein X=H or amino acid,
Y=OH or amino acid.

In U.S. Pat. No. 4,683,291, inhibition of platelet function is disclosed with synthetic peptides designed to be high affinity antagonists of fibrinogen binding to platelets. These synthetic peptides have up to 16 amino acid residues with Arg-Gly-Asp-Val or
Arg-Gly-Asp-Ser at the C-terminal.

Similar synthetic peptides which contain the Arg-Gly-Asp sequence and their use as inhibitors of fibrinogen binding to platelets are disclosed by Kloczewiak et al., *Biochem.* 23, 1767–1774 (1984); Plow et al., *Proc. Natl. Acad. Sci.* 82, 8057–8061 (1985); Ruggeri et al., Ibid. 83, 5708–5712 (1986); Ginsberg et al., *J. Biol. Chem.* 260 (7), 3931–3936 (1985); and Haverstick et al., Blood 66 (4), 946–952 (1985).

BRIEF DESCRIPTION OF THE INVENTION

In accordance with the present invention novel tetrapeptide derivatives are provided which have useful activity as inhibitors of platelet aggregation. They are believed to act by antagonizing interactions between fibrinogen and/or extracellular matrix proteins and the platelet gpIIb/IIIa receptor. These tetrapeptide derivatives contain the sequence X-Gly-Asp-Y (I)

$$\text{wherein } X = H_2N\overset{\overset{\displaystyle NH}{\|}}{C}-NH-(CH_2)_n-\overset{\overset{\displaystyle Z}{|}}{CH}-COOH \text{ or } Ac-Arg,$$

Z=H, $NH_2$ or NH-Acyl,
n=1 to 4, $$\text{wherein } Y = H_2N-\overset{\overset{\displaystyle R_1}{|}}{\underset{\underset{\displaystyle R_3}{|}}{\underset{\displaystyle (CH_2)_m}{|}}{C}}-R_2, \text{ Tyr}-NH_2 \text{ or Phe}-NH_2,$$

$R_1$=H, alkyl, phenyl or phenylalkyl,
$R_2$=H, COOH, $CONH_2$, $COCH_3$, $CH_2OH$, $CH_2NH_2$, $C(NH)CH_3$ or $C(NH)NH_2$,
$R_3$=phenyl, biphenyl or naphthyl, each substituted with 1 to 3 alkyl or alkoxy groups, or an unsubstituted naphthyl, biphenyl or pyridyl group,
m=0 to 2, wherein alkyl and alkoxy each have 1 to 4 carbons, provided that when Y is Tyr-$NH_2$ or Phe-$NH_2$, X is Ac-Arg, and provided further that when Z is $NH_2$ or NH-Acyl, X is in the D- or L-amino acid stereo-configuration. In the above general formula (I), X and Y are attached to glycine and aspartic acid, respectively, through conventional peptide bonds, with the N-terminal shown at the left and the C-terminal at the right.

It will be seen that X in the above formula is arginine when Z=$NH_2$ and n=3; homoarginine when Z=$NH_2$ and n=4; and guanidinobutyric acid when Z=H and n=2. Alternatively, this α-$NH_2$ of arginine can be replaced with H or N-acyl, preferably N-acetyl. The methylene chain can range from one to four units, as shown, but preferably is three $CH_2$ units in length.

It will also be seen that Y in the above formula (I) generally is an unnatural aromatic amino acid derivative, preferably a tyrosine derivative in which the C-terminal is H, COOH, $CONH_2$, $COCH_3$, $CH_2OH$, $CH_2NH_2$, $C(NH)CH_3$ or $C(NH)NH_2$, and the aromatic or benzenoid ring is substituted with one to three lower alkyl or alkoxy groups. The lower alkyl substituents in the general formula (I) can be, for example, methyl, ethyl, iso-propyl or butyl.

A most preferred compound is Arg-Gly-Asp-(O-methyltyrosine)-amide:

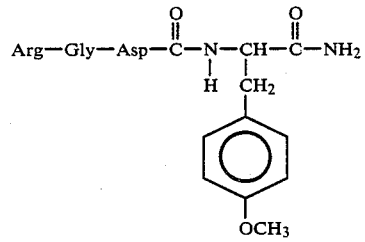

This compound, in which the p-hydroxyphenyl group of tyrosine is methylated and the C-terminal is carboxyamide, unexpectedly is substantially more active as an initiator of platelet aggregation than either Arg-Gly-Asp-Ser or Arg-Gly-Asp-Tyr. This advantage has been demonstrated in platelet-rich plasma assays and with in vivo assays where, by comparison, Arg-Gly-Asp-Ser is relatively ineffective. Moreover, Arg-Gly-Asp-(O-methyltyrosine)-amide is effective in preventing thrombosis in a rat carotid artery assay model, thereby demonstrating its use as an antithrombotic agent.

In those instances where the C-terminal amino acid Y in the above formula (I) is a natural amino acid, it is an amide derivative of tyrosine or phenylalanine and the NH$_2$-terminal amino acid X is acetyl-arginine. Thus, it has been surprisingly found that acetyl-RGDY-amide is very effective in the in vivo thrombocytopenia assay (85% inhibition) whereas the non-acetylated RGDY-amide is relatively ineffective (only 19% inhibition).

Other preferred compounds of the invention are Arg-Gly-Asp-(O-ethyltyrosine)-amide, des-amino-Arg-Gly-Asp-(O-methyltyrosine)-amide, des-amino-(homoarginine)-Gly-Asp-(O-methyltyrosine)-amide, acetyl-Arg-Gly-Asp-(O-methyltyrosine)-amide, acetyl-(D-Arg)-Gly-Asp-(O-methyltyrosine)-amide, Arg-Gly-Asp-(4-methoxy-1-naphthylalanine)-amide, Arg-Gly-Asp-(2,6-dimethyl-O-methyltyrosine)amide, and Arg-Gly-Asp-(p-phenyl-phenylalanine)-amide.

DETAILED DESCRIPTION OF THE INVENTION

The novel peptides of this invention can be made by conventional methods of peptide synthesis. A preferred method is the solid phase synthesis of Merrifield, *J. Amer. Chem. Soc.* 85, 2149–2154 (1963); *Science* 150, 178–185 (1965); Ibid., 232, 341–347 (1986).

Solid phase synthesis is generally commenced from the C-terminus of the peptide by coupling a protected alpha amino acid to a suitable resin, e.g., chloromethylated polystyrene resin or p-methylbenzhydrylamine resin when synthesizing a peptide amide derivative. In the present invention, the tyrosine derivative as described above can be used as the C-terminal peptide for initiating the solid phase synthesis. The three remaining alpha amino acids are then coupled stepwise in the desired order to obtain an intermediate peptide coupled to the resin. During this synthesis, suitable protecting groups are used as needed. Thus, aspartic acid is protected on the β-carboxyl group as the benzyl ester and arginine is protected on the guanidino group by tosyl. Each α-amino group is protected with the t-butyloxycarbonyl group (BOC).

After the desired tetrapeptide sequence has been completed, the intermediate peptide is cleaved from the resin and protecting groups are removed by treatment with a reagent such as HF. The peptide can then be purified by high performance liquid chromatography (HPLC) or other such methods of protein purification.

Background information on the established solid phase synthesis procedure which can be used for the preparation of the tetrapeptide derivatives herein can be had by reference to the treatise by Stewart and Young, "Solid Phase Peptide Synthesis," W. H. Freeman & Co., San Francisco, 1969, and the review chapter by Merrifield in *Advances in Enzymology* 32, pp. 221–296, F. F. Nold, Ed., Interscience Publishers, New York, 1969; and Erickson and Merrifield, *The Proteins*, Vol. 2, p. 255 et seq. (ed. Neurath and Hill), Academic Press, New York, 1976.

As used herein, the peptide sequences are shown by conventional single or three letter abbreviations for the constituent amino acids as follows:

| Abbreviated Designation | | Amino Acid |
|---|---|---|
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| *Y | Tyr | Tyrosine |

*Not to be confused with the C-terminal Y in the general formula (I) for the tetrapeptide derivatives as defined herein.

The platelet-binding inhibitor activity of the peptide derivatives of this invention is demonstrated by various assays. In one assay, the peptides are tested for their inhibition of thrombin-induced platelet aggregation in washed human platelets. The % inhibition is determined for the test peptide by comparing the extent of platelet aggregation in the presence and absence of the peptide.

In another assay, platelet aggregation is examined in platelet-rich plasma which also is rich in fibrinogen and other plasma proteins.

In yet another test, the effect of the peptide on collagen induced thrombocytopenia (platelet aggregation) is measured in vivo in the art. Again, the % inhibition is determined for the test peptide and compared against a saline or ethanol vehicle in the absence of peptide.

In these assays, the test compound results were then compared with the activity of the known active inhibitor tetrapeptide Arg-Gly-Asp-Ser.

Finally, a most preferred compound of this invention was tested in a rat carotid artery thrombosis bioassay. In this test, a thrombus is induced to form in a rat carotid artery by applying an electrical current to the artery for 5 minutes. In the presence of infused saline, a clot forms and occludes the artery in about 8–9 minutes. Infusion of the preferred inhibitor compound of this invention, Arg-Gly-Asp-(O-methyltyrosine)-amide, significantly delayed or prevented occlusion whereas, by comparison, infusion of the known inhibitor Arg-Gly-Asp-Ser lengthened the time to occlusion only slightly.

The following examples will further illustrate the invention in greater detail although it will be appreciated that the invention is not limited to these specific examples.

EXAMPLE 1

The novel peptide derivatives of this invention were made by conventional solid phase synthesis. This synthesis is illustrated by preparation of Arg-Gly-Asp-(O-methyltyrosine)-NH$_2$ as follows:

20 grams of p-methylbenzhydryl amine resin (containing 14 mmoles of amino groups) was shaken with 2 equivalents (eq.) of BOC-tyrosine methyl ether and 2 eq. of dicyclohexyl carbodiimide (DCC) in methylene chloride for 4 hours. The resin was filtered and washed repeatedly, with dimethylformamide (DMF), followed by methanol and then methylene chloride. The BOC group was removed by treatment with 50% trifluoroacetic acid (TFA) in methylene chloride for 30 minutes and the resin was washed with methylene chloride, neutralized with 10% diisopropylamine and washed again. The resin was then ready for reaction with 2 eq. of the next amino acid, BOC-β-benzyl-aspartic acid. The cycle as above described was repeated for each amino acid except that 2 eq. of hydroxybenzotriazole was added to the BOC-tosylarginine and DCC.

The resulting tetrapeptide was removed from 10.0 grams of resin and deprotected with 88 ml. of 10% anisole in liquid HF at 0° C., and following evaporation of the HF, the peptide was taken up in 30% aqueous acetic acid and lyophilized. The peptide product was purified by HPLC on a 700 ml. column of 15-20 μm (300 Å) Vydac $C_{18}$ reverse phase packing (The Separations Group, Hesperia, Calif.) using a 0-50% gradient in acetonitrile (0.1% TFA). Fractions containing product, as ascertained by analytical HPLC, were pooled and lyophilized to afford about 1.0 gram of pure tetrapeptide from 10 grams of resin.

Substantially similar synthesis procedures were used for the solid phase synthesis of other peptide derivatives of this invention by substituting equivalent amounts of other BOC-tyrosine derivatives for the BOC-tyrosine methyl ether, and/or des-amino arginine, homoarginine or acetyl arginine for arginine in the above example.

EXAMPLE 2

The peptide derivatives prepared in Example 1 were tested for their platelet-binding inhibitor activity by the following standard protocol:

Inhibition of Thrombin-Induced Platelet Aggregation in Washed Human Platelets Platelet Preparation: 60 ml of whole blood is freshley drawn and anticoagulated with 1/10th volume of CCD (100 mM Na Citrate and 136 mM glucose, pH 6.5 with HCl) at room temperature (RT). The blood is divided into 2 disposable 60 ml plastic centrifuge tubes and centrifuged for 3 minutes at 1000×g, allowing the centrifuge to coast to a stop (no brake). The platelet rich plasma (PRP) is withdrawn, being careful that no white cells are taken and is placed in a 60 ml centrifuge tube. The tube is immediately placed on ice for 15 minutes. After the 15 minutes at 0° C., ½ volume of ice cold CCD is added (i.e. 15 ml CCD/30 ml of PRP). The tube is mixed and the contents are divided equally into two centrifuge tubes. These are then centrifuged at 0° C. for 10 minutes at 900×g (no brake). The supernatant is carefully poured off. The platelet pellet is gently resuspended in ½ the original volume of PRP in a 0° C. modified Tangen-Hepes-BSA buffer, pH 7.4, consisting of 145 mM NaCl, 5 mM KCl, 0.05 mM $CaCl_2$, 0.1 mM $MgCl_2$, 11 mM glucose, 15 mM Hepes (N-2-hydroxyethylpiperazine-N'-2-ethanesulfonic acid), 1 mg/ml bovine serum albumin, (pH adjusted with NaOH). The resuspended pellets are combined into 1 centrifuge tube and incubated undisturbed at 37° C. for 30 minutes. After the incubation, the platelet suspension is removed and an aliquot is quickly counted in a hemocytometer or a Coulter® Counter (Coulter Electronics, Hialeah, Fla.). The platelet count is adjusted to $3 \times 10^8$ cells/ml with the Tangen-Hepes-BSA buffer.

Compound Testing: Aggregation studies are accomplished using a Payton aggregometer (Payton Scientific, Inc., Buffalo, N.Y.). The control compound used was RGDS (Arg-Gly-Asp-Ser) purchased from Peninsula Laboratories, Calif.; the thrombin was purchased from Parke-Davis, N.J. and prepared at a working concentration of 0.5 units/ml with the Tangen-Hepes-BSA buffer supplemented with 16 mM $CaCl_2$, 16 mM $MgCl_2$. All compounds are diluted to a working concentration of $10^{-3}$M with double distilled water. The reaction mixture consisted of 400 μl of $3 \times 10^8$/ml washed platelets, 50 μl of buffer (control) or test compound at $10^{-3}$M with a final concentration of $10^{-4}$M. Platelets, test compound or buffer are placed in cuvettes in the aggregometer for a 1 minute preincubation before adding thrombin. 50 μl of 0.5 U/ml thrombin is added to cuvettes and the aggregation is monitored for 1 minute, which is the time for maximal aggregation of the platelets. All compounds are run in duplicate. The entire test is run within 3 hours, since this is the maximal viability of the platlets. Results are calculated as follows: % of control=[(maximal OD minus initial OD of compound) divided by (maximal OD minus initial OD of control)]×100. % inhibition=100 minus (% of control).

The compounds tested and their activity results in % inhibition at $10^{-4}$M and $IC_{50}$'s were as recorded in Table I. $IC_{50}$'s (if a compound showed 50% inhibition) were calculated by linear regression of the dose response curve.

TABLE I

| No. | Peptide Sequence | % Inhibition at $10^{-4}$ M | $IC_{50}(M)$ |
|---|---|---|---|
| 1 | RGDS | 71 | $4 \times 10^{-5}$ |
| 2 | GRGDSP—$NH_2$ | 55 | $8 \times 10^{-5}$ |
| 3 | RGDY—$NH_2$ | 45 | — |
| 4 | Ac—RGDY—$NH_2$ | 68 | $5 \times 10^{-5}$ |
| 5 | RGDF—$NH_2$ | 77 | $1 \times 10^{-5}$ |
| 6 | RGD(O—methyl-Tyr)—$NH_2$ | 79 | $2 \times 10^{-5}$ |
| 7 | RGD(O—ethyl-Tyr)—$NH_2$ | 54 | — |
| 8 | Ac—RGD(O—methyl-Tyr)—$NH_2$ | 78 | $2 \times 10^{-5}$ |
| 9 | RGD(2,6-dimethyl-O—methyl-Tyr)—$NH_2$ | 78 | $2 \times 10^{-5}$ |
| 10 | des-$NH_2$—RGD(O—methyl-Tyr-)—$NH_2$ | 90 | $1 \times 10^{-5}$ |
| 11 | des-$NH_2$—(homo Arg)—GD—(O—methyl-Tyr)—$NH_2$ | 82 | $1 \times 10^{-5}$ |

Ac = Acetyl

EXAMPLE 3

Several peptide derivatives prepared in Example 1 were further tested for their platelet-binding in platelet-rich plasma (PRP) by the following standard protocol:

In-Vitro Human Platelet Aggregation in PRP

Healthy male or female donors who have not taken any antiplatelet drugs for at least 2 weeks were fasted for 8 hours prior to drawing blood; then 30 ml whole blood was collected using a butterfly needle and 30 cc plastic syringe with 3 ml of 0.129M buffered sodium citrate (3.8%). The syringe is rotated carefully as blood is being drawn to mix the citrate. Platelet-rich plasma (PRP) is prepared by centrifugation at 100×g for 10 minutes at room temperature, allowing the centrifuge to coast to a stop without braking. The PRP is removed from the blood with a plastic pipette and placed in a plastic, capped, 50 ml Corning conical sterile centrifuge tube. The tube is capped and placed at room temperature. Platelet poor plasma (PPP) is prepared by centrifuging the remaining blood at 2000×g for 15 minutes at room temperature allowing the centrifuge to coast to a stop without braking. The PRP is adjusted with PPP to a count of $2-3\times10^8$ platelets per ml. 400 µl of the PRP preparation and 50 µl of the compound to be tested or saline were preincubated for 1 minute at 37° C. in a Payton aggregometer (Payton Scientific, Inc., Buffalo, NY). 50 µl of adenosine 5'diphosphate (ADP) (50 µM) is added to the cuvettes and the aggregation is monitored for 1 minute. All compounds are tested in duplicate. The entire procedure is run within 3 hours, since this is the maximal viability of the platelets. The saline instead of compound is used to determine the maximal aggregation. Results are calculated as follows: Percent of control=[(maximal OD minus initial OD of compound) divided by (maximal OD minus initial OD of control)]×100. % inhibition=100−(percent of control).

The compounds tested and their activity results in % inhibition at $10^{-4}$M and IC$_{50}$'s were as recorded in Table II. IC$_{50}$'s (if a compound showed 50% inhibition) were calculated by linear regression of the dose response curve.

TABLE II

| No. | Peptide Sequence | % Inhibition at $10^{-4}$ M | IC$_{50}$(M) |
|---|---|---|---|
| 1 | RGDS | 25 | $3\times10^{-4}$ |
| 2 | GRGDSP—NH$_2$ | 23 | $2\times10^{-4}$ |
| 3 | RGDF—NH$_2$ | 100 | $2\times10^{-5}$ |
| 4 | Ac—RGDY—NH$_2$ | 48 | — |
| 5 | RGD(O—methyl-Tyr)—NH$_2$ | 100 | $3\times10^{-5}$ |
| 6 | Ac—RGD(O—methyl-Tyr)—NH$_2$ | 100 | $2\times10^{-5}$ |
| 7 | RGD(2,6-dimethyl-O—methyl-Tyr)—NH$_2$ | 53 | $9\times10^{-5}$ |
| 8 | des-NH$_2$—RGD(O—methyl-Tyr)—NH$_2$ | 100 | $2\times10^{-5}$ |
| 9 | des-NH$_2$—(homo Arg)GD-(O—methyl-Tyr)—NH$_2$ | 100 | $2\times10^{-5}$ |
| 10 | RGD(4-methoxy-1-naphthyl-Ala)—NH$_2$ | 100 | $1\times10^{-5}$ |
| 11 | des-NH$_2$—RGD(O—methyltyramine)—NH$_2$ | 100 | $2\times10^{-5}$ |
| 12 | Ac—(D-Arg)GD(O—methyl-Tyr)—NH$_2$ | 71 | — |
| 13 | RGD(p-phenyl-Phe)—NH$_2$ | 100 | — |

From the above results in Table II it will be seen that compounds 4 to 13 were from 2 to 4 times as effective in % inhibition of platelet aggregation in platelet-rich plasma in vitro compared to the control compound Nos. 1 and 2. While compound 3 also was effective in this in vitro test, it was less effective in the in vivo test of Example 4, below.

EXAMPLE 4

Several peptide derivatives prepared in Example 1 were further tested for their effect on collagen induced thrombocytopenia in vivo in the rat as follows:

In Vivo Rat Thrombocytopenia

Male rats (Charles River, CRL:CD(SD), 400–450 g) were used. The rats were anesthetized with Na pentabarbital (65 mg/kg, Vet Labs, Limited, Inc., Lenexa, KA). Two incisions were made to expose both jugular veins. Using an infusion pump (Harvard Apparatus, South Natick, Mass.) and a 5 cc syringe with a 19 g. butterfly, the test compound or vehicle was infused into the left jugular vein at a rate of 0.39 ml/min for 3 min. After 2 min of compound/vehicle infusion, collagen (60 µg/kg) (Helena Laboratories, Beaumont, TX) was injected with a 1 ml syringe into the right jugular vein. The body cavity was opened and the vena cava was exposed for blood sampling. One min after the collagen injection, compound infusion was stopped and blood was sampled from the vena cava (within 30 sec) with a 3 cc syringe containing 0.3 mg of 4.5% EDTA/Tris (0.1M) (pH 7.35) plus 150 µM indomethacin. Platelet rich plasma (PRP) was prepared by centrifuging the blood at 126×g for 10 min. Five µl of PRP was counted in 20 ml of Isoton ® III in a Coulter Counter. Percent inhibition of collagen induced aggregation was calculated by comparison of the number of platelets counted in treated animals with numbers for animals receiving no collagen and with counts from animals receiving vehicle and collagen. Estimation of potency was based on inhibition of collagen-induced thrombocytopenia.

The % inhibition of platelet aggregation in vivo and the maximum inhibition % of the test compounds is set forth in the following Table III. Four animals were tested with each compound to give the data shown.

TABLE III

| No. | Peptide Sequence | % Inhibition at 1 mg/kg | Maximum Inhibition % |
|---|---|---|---|
| 1 | RGDS | 29 ± 6 | 30 |
| 2 | GRGDSP—NH$_2$ | 18 ± 3 | 20 |
| 3 | RGDY—NH$_2$ | 19 ± 12 | 20 |
| 4 | RGDF—NH$_2$ | 40 | — |
| 5 | Ac—RGDY—NH$_2$ | 85 | — |
| 6 | RGD(O—methyl Tyr)—NH$_2$ | 75 ± 4 | 80 |
| 7 | Ac—RGD(O—methyl-Tyr)—NH$_2$ | 86 | — |
| 8 | RGD(2,6-dimethyl-O—methyl-Tyr)—NH$_2$ | 70 | — |
| 9 | des-NH$_2$—RGD(O—methyl-Tyr)—NH$_2$ | 64 | — |
| 10 | des-NH$_2$—(homo Arg)GD—(O—methyl-Tyr)—NH$_2$ | 60 | — |

From the above results in Table III it will be seen that preferred compounds of the invention (Nos. 5 to 10) were from about 2 to 4 times as effective in % inhibition of platelet aggregation in vivo compared to the control compound Nos. 1 to 3. Compound 4 had intermediate effectiveness.

EXAMPLE 5

The tetrapeptide derivative Arg-Gly-Asp-(O-methyltyrosine)-amide was still further tested for its activity against rat carotid artery thrombosis as follows:

Rat Carotid Artery Thrombosis

Male Sprague-Dawley rats (300–450 gms) are anesthetized with sodium pentabarbital i.p. 30 mg/kg. A mid-line incision is made in the neck through which the trachea, jugular vein and carotid artery are exposed and isolated. The trachea is cannulated and the animal is allowed to breathe $O_2$ enriched room air. The jugular vein is cannulated for i.v. infusion. The carotid artery is stripped of its sheath and all vagal fibers for a distance of 1.5–2.0 cm and fitted on the proximal end with an appropriately sized Carolina Medical Electronics electro magnetic flow probe. Recording of blood flow is done on a Gould recorder via the Carolina Medical Electronics flow meter. A mechanical zero flow is determined by momentarily clamping the artery distal to the flow probe. A few millimeters distal to the flow probe, a bipolar electrode is placed on the artery and positioned so that it touches only the artery.

After 15 minutes for stabilization after the surgical preparation, an i.v. infusion of the desired dose of peptide is begun into the jugular vein (using a Harvard infusion pump) and allowed to run for 5 minutes at which time the flowmeter is turned off and an electrical current of 2.5 mA is applied to the external arterial wall (Grass stimulator and constant current unit) for 5 minutes. The infusion of peptide is allowed to run throughout the test time period of 30 minutes.

Immediately after discontinuing the electrical current the flow meter is turned on and measurements of flow amplitude are taken. At the point of a 20% decrease in systolic flow, thrombus formation has begun and the time from end of current to 20% flow decrease is noted. This is the "time in minutes to onset of thrombus formation." When flow declines to the predetermined 0 flow, time in minutes from onset of thrombus is noted and this time is called "Time in minutes to 0 flow from onset of thrombus." The sum of these times is "time from injury to 0 flow." The latter time (or time to occlusion) for the test compound compared to that of the known inhibitor Arg-Gly-Asp-Ser is set forth in the following Table IV.

TABLE IV

| Peptide (Dose infused) | Number of Animals | Time to Occlusion (minutes) |
|---|---|---|
| Saline | 6 | 8.9 ± 0.8 |
| RGDS | | |
| (0.05 mg/kg/min.) | 6 | 13 ± 1 |
| (1.0 mg/kg/min.) | 6 | 12 ± 2 |
| RGD (O—methyl-Tyr)—NH$_2$ | | |
| (1.0 mg/kg/min.) | 4 | 15 (with 2 animals) ∞* (with 2 animals) |

*Occlusion did not occur even 30 minutes after infusion was stopped.

The novel tetrapeptide derivatives of this invention can be used for administration to humans by conventional means, preferably in formulations with pharmaceutically acceptable diluents or carriers. The preferable route of administration as a platelet aggregation inhibitor is parenteral, especially intravenous. Intravenous administration of the tetrapeptide derivatives in solution with normal physiological saline, human albumin and other such diluents and carriers is illustrative. Other suitable formulations of the active tetrapeptide derivatives in pharmaceutically acceptable diluents and carriers in therapeutic dosage form can be prepared by reference to general texts in the pharmaceutical field such as, for example, *Remington's Pharmaceutical Sciences*, Ed. Arthur Osol, 16th ed., 1980, Mack Publishing Co., Easton, Pa.

Various other examples will be apparent to the person skilled in the art after reading the present disclosure without departing from the spirit and scope of the invention. It is intended that all such examples be included with the scope of the appended claims.

What is claimed is:

1. A tetrapeptide derivative having inhibitory activity toward platelet aggregation selected from the group consisting of X-Gly-Asp-Y

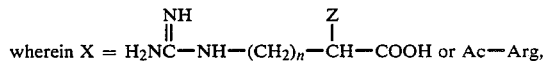

$Z = H$, $NH_2$ or NH-Acyl,
$n = 1$ to 4,

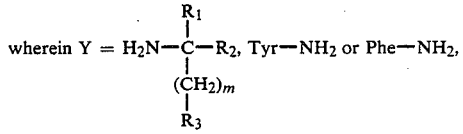

$R_1 = H$, alkyl, phenyl or phenylalkyl,
$R_2 = H$, COOH, CONH$_2$, COCH$_3$, CH$_2$OH, CH$_2$NH$_2$, C(NH)CH$_3$ or C(NH)NH$_2$,
$R_3 =$ phenyl, unsubstituted biphenyl or naphthyl, each substituted with 1 to 3 alkyl or alkoxy groups, or an unsubstituted naphthyl, biphenyl or unsubstituted pyridyl group,
$m = 0$ to 2,
wherein alkyl and alkoxy each have 1 to 4 carbons, provided that when Y is Tyr-NH$_2$ or Phe-NH$_2$, X is Acetyl-Arg, and provided further that when Z is NH$_2$ or NH-Acyl, X is in the D- or L-amino acid stereo-configuration.

2. The tetrapeptide derivative of claim 1 having the sequence Arg-Gly-Asp-(O-methyltyrosine)-amide.

3. The tetrapeptide derivative of claim 1 having the sequence Arg-Gly-Asp-(O-ethyltyrosine)-amide.

4. The tetrapeptide derivative of claim 1 having the sequence acetyl-Arg-Gly-Asp-(O-methyl tyrosine)-amide.

5. The tetrapeptide derivative of claim 1 having the sequence acetyl-(D-Arg)-Gly-Asp-O-methyltyrosine)-amide.

6. The tetrapeptide derivative of claim 1 having the sequence Arg-Gly-Asp-(4-methoxy-1-naphthylalanine)-amide.

7. The tetrapeptide derivative of claim 1 having the sequence Arg-Gly-Asp-(2,6-dimethyl-O-methyltyrosine)-amide.

8. The tetrapeptide derivative of claim 1 having the sequence desamino-Arg-Gly-Asp-(O-methyltyrosine)-amide.

9. The tetrapeptide derivative of claim 1 having the sequence desamino-(homoarginine)-Gly-Asp-(O-methyl-tyrosine)-amide.

10. The tetrapeptide derivative of claim 1 having the sequence Arg-Gly-Asp-(p-phenyl-phenylalanine)-amide.

11. The tetrapeptide derivative of claim 1 having the sequence acetyl-Arg-Gly-Asp-Tyr-amide.

12. The method of inhibiting platelet aggregation in a warm blooded mammal comprising administering to said mammal an effective amount of the tetrapeptide derivative of claim 1 in a pharmaceutically acceptable carrier.

13. The method of claim 12 in which the tetrapeptide derivative has the sequence Arg-Gly-Asp-(O-methyl-tyrosine)-amide.

14. The method of inhibiting formation of a thrombus in a warm blooded mammal comprising administering to said mammal an effective amount of the tetrapeptide derivative of claim 1 in a pharmaceutically acceptable carrier.

15. The method of claim 14 in which the tetrapeptide derivative has the sequence Arg-Gly-Asp-(O-methyl-tyrosine)-amide.

16. A pharmaceutical composition comprising the tetrapeptide derivative of claim 1 in a pharmaceutically acceptable carrier.

* * * * *